United States Patent
Büschken et al.

(10) Patent No.: US 7,683,204 B2
(45) Date of Patent: Mar. 23, 2010

(54) MIXTURE OF ALICYCLIC POLYCARBOXYLIC ACID ESTERS HAVING HIGH CIS ISOMER CONTENT

(75) Inventors: Wilfried Büschken, Haltern am See (DE); Michael Graβ, Haltern am See (DE); Alfred Kaizik, Marl (DE); Dietrich Maschmeyer, Recklinghausen (DE); Axel Tuchlenski, Mülheim (DE); Franz Nierlich, Marl (DE)

(73) Assignee: Oxeno Olefinchemie GmbH, Marl (DE)

( * ) Notice: Subject to any disclaimer, the term of this patent is extended or adjusted under 35 U.S.C. 154(b) by 1500 days.

(21) Appl. No.: 10/489,317

(22) PCT Filed: Aug. 30, 2002

(86) PCT No.: PCT/EP02/09732

§ 371 (c)(1),
(2), (4) Date: Aug. 11, 2004

(87) PCT Pub. No.: WO03/029168

PCT Pub. Date: Apr. 10, 2003

(65) Prior Publication Data

US 2004/0260113 A1    Dec. 23, 2004

(30) Foreign Application Priority Data

Sep. 24, 2001    (DE) ............................ 101 46 848

(51) Int. Cl.
*C07C 69/74* (2006.01)
(52) U.S. Cl. .................................... 560/127
(58) Field of Classification Search ............... 560/127
See application file for complete search history.

(56) References Cited

U.S. PATENT DOCUMENTS

| | | | | |
|---|---|---|---|---|
| 3,027,398 A | * | 3/1962 | Foohey | 560/127 |
| 3,334,149 A | * | 8/1967 | Akin et al. | 568/831 |
| 5,614,486 A | * | 3/1997 | Giersch et al. | 512/21 |
| 2004/0097773 A1 | | 5/2004 | Beckmann et al. | |
| 2006/0036121 A1 | | 2/2006 | Kaizik et al. | |
| 2006/0167151 A1 | | 7/2006 | Grass et al. | |
| 2007/0060768 A1 | | 3/2007 | Grass et al. | |

FOREIGN PATENT DOCUMENTS

WO    00/78704    12/2000

OTHER PUBLICATIONS

U.S. Appl. No. 10/511,595, filed Nov. 2, 2004, Grass et al.
U.S. Appl. No. 10/579,471, filed May 15, 2006, Zanthoff, et al.
U.S. Appl. No. 10/519,413, filed Jan. 6, 2005, Grass, et al.
Samuel Siegel, et al., "The stereochemistry of hydrogenation of isomers of methyl tetrahydrophthalate and methyl phthalate", J. Am. Chem. Soc., vol. 81, pp. 3655-3658, Jul. 20, 1959.
U.S. Appl. No. 11/739,345, filed Apr. 24, 2007, Grass, et al.
U.S. Appl. No. 11/622,567, filed Jan. 12, 2007, Grass, et al.
U.S. Appl. No. 11/911,691, Oct. 16, 2007, Grass, et al.

* cited by examiner

*Primary Examiner*—Taylor Victor Oh
(74) *Attorney, Agent, or Firm*—Oblon, Spivak, McClelland, Maier & Neustadt, L.L.P.

(57) ABSTRACT

The present invention relates to mixtures of alicyclic polycarboxylic esters with high cis content, to a process for their preparation by ring-hydrogenation of the corresponding aromatic polycarboxylic esters, and also to the use of the mixtures.

5 Claims, No Drawings

MIXTURE OF ALICYCLIC POLYCARBOXYLIC ACID ESTERS HAVING HIGH CIS ISOMER CONTENT

The present invention relates to mixtures of alicyclic polycarboxylic esters with high cis content, to a process for their preparation by ring-hydrogenation of the corresponding aromatic polycarboxylic esters, and also to the use of the mixtures.

Alicyclic polycarboxylic esters, such as the esters of cyclohexane-1,2-dicarboxylic acid, are used as a component of lubricating oil and as auxiliaries in metalworking. They are also used as plasticizers for polyolefins.

For plasticizing PVC it is currently mainly esters of phthalic acid that are used, for example dibutyl, dioctyl, dinonyl, or didecyl esters. Since these phthalates have recently been described as hazardous to health, there is a risk that their use in plastics could become restricted. Alicyclic polycarboxylic esters, some of which have been described in the literature as plasticizers for various plastics, could then be available as suitable replacements, although with a somewhat different performance profile.

The most economic route to preparation of alicyclic polycarboxylic esters in most cases is ring-hydrogenation of the corresponding aromatic polycarboxylic esters, for example of the abovementioned phthalates. Some processes for this purpose have been disclosed:

U.S. Pat. No. 5,286,898 and U.S. Pat. No. 5,319,129 describe a process which can hydrogenate dimethyl terephthalate on supported Pd catalysts doped with Ni or with Pt and/or with Ru, at temperatures of 140° C. or above and at a pressure of from 50 to 170 bar, to give the corresponding dimethyl hexahydroterephthalate.

DE 28 23 165 hydrogenates aromatic carboxylic esters on supported Ni, Ru, Rh, and/or Pd catalysts to give the corresponding alicyclic carboxylic esters at from 70 to 250° C. and from 30 to 200 bar. U.S. Pat. No. 3,027,398 discloses the hydrogenation of dimethyl terephthalate on supported Ru catalysts at from 110 to 140° C. and from 35 to 105 bar.

WO 00/78704 discloses a process for hydrogenating benzenepolycarboxylic esters to give the corresponding alicyclic compounds. Here, use is made of supported catalysts which comprise a metal of the 8th transition group alone or together with at least one metal of the 1st or 7th transition group of the Periodic Table and have 50% of macropores. Ruthenium is used as preferred metal of the 8th transition group.

The ring-hydrogenation of aromatic polycarboxylic esters can produce at least two isomers with respect to the ring system and to the ester functions.

For example, the products from the hydrogenation of phthalic diesters (benzene-1,2-dicarboxylic diesters) are cis- and/or trans-cyclohexane-1,2-dicarboxylic diesters. The cis diester here is the isomer in which one ester group has axial (a) orientation and the other has equatorial (e) orientation. The trans compound is the isomer in which both ester groups have either axial (a, a) or equatorial (e, e) orientation.

Hydrogenation of isophthalic diesters (benzene-1,3-dicarboxylic diesters) can produce cis- and trans-cyclohexane-1,3-dicarboxylic diesters. In the cis compound the ester groups have either axial-axial (a, a) or equatorial-equatorial (e, e) orientation. In the trans compound one ester group has axial orientation and the other has equatorial orientation.

The hydrogenation of terephthalic diesters (benzene-1,4-dicarboxylic diesters) can produce cis- and trans-cyclohexane-1,4-dicarboxylic diesters. Here, in the cis compound one ester group has axial orientation and the other has equatorial orientation (a, e). In the trans compound both ester groups have either axial (a, a) or equatorial (e, e) orientation.

In the case of alicyclic polycarboxylic esters having more than two substituents on the same ring system, each substituent can have cis or trans configuration with respect to another substituent. For the purposes of the present invention, all compounds in which the majority of the ester groups have transconfiguration with respect to one another are to be regarded as trans compounds, irrespective of the other configurations of the substituents with respect to one another.

The literature gives only sparse and incomplete information concerning the configuration of the products which are produced during the ring-hydrogenation of aromatic polycarboxylic esters.

For example, according to U.S. Pat. No. 3,027,165 the hydrogenation of dimethyl terephthalate on a ruthenium catalyst produces a mixture of dimethyl cis- and trans-cyclohexane-1,4-dicarboxylates with a melting point below 20° C. It is known that the melting point of the trans diester is 70° C. and that the melting point of the cis diester is 7° C. Assuming conventional melting behavior (no mixed crystal formation), i.e. that starting from one pure isomer and adding the other isomer, the melting point of the mixture falls until the eutectic point has been reached, it is possible to estimate that the hydrogenation mixture is composed mainly of dimethyl cis-cyclohexane-1,4-dicarboxylate.

S. Siegel and G. McCaleb in JACS, 81, 1959, pp. 3655-3658 describe the hydrogenation of dimethyl phthalates on suspended platinum oxide powder in glacial acetic acid. Irrespective of the pressure and concentration, the mixtures obtained of the corresponding cyclohexanoic acid derivatives have practically 100 mol % cis content. The yields of the esters isolated are not mentioned. This hydrogenation method has some disadvantages: the catalyst has to be separated off from the hydrogenation mixture, and experience has shown that losses of catalyst are unavoidable here. The solvent used, glacial acetic acid, is highly corrosive and therefore requires apparatus made from high-performance materials. In addition, the glacial acetic acid, which makes up from 80 to 90% of the hydrogenation discharge, has to be separated off from the target product.

The preparation of dimethyl cyclohexanedicarboxylates with high cis content is therefore known. However, that publication does not disclose whether other carboxylic esters with high cis content are also accessible via the published method or any other method.

If the ruthenium-containing catalysts disclosed in WO 00/78704 are used for the hydrogenation of diisononyl phthalates, the product mixture obtained has about 93 mol % of cis isomer and correspondingly 7 mol % of the trans isomer.

There are therefore no known alicyclic polycarboxylic ester mixtures with above 93 mol % content of the cis isomer(s), with the exception of methyl cyclohexanedicarboxylates.

It was therefore an object of the present invention to prepare mixtures of this type and to test their use as plasticizers for plastics.

The invention therefore provides alicyclic polycarboxylic ester mixtures, with the exception of methyl cyclohexanedicarboxylates, comprising at least two isomers with respect to the position of the ester groups on the ring system, where the proportion of the cis isomers is above 93 mol %.

The mixtures of the invention are preferably prepared by hydrogenating the corresponding aromatic polycarboxylic esters. For this, use may be made of a catalyst which comprises at least one precious metal of the 8th transition group of the elements and comprises at least one metal of the 2nd transition group of the Periodic Table.

The present invention also provides a process for preparing alicyclic polycarboxylic ester mixtures which have at least two isomers with respect to the position of the ester groups on the ring system, and which have a proportion of the cis isomer above 93 mol %, by catalytic hydrogenation of the corresponding aromatic polycarboxylic esters, where the catalyst comprises at least one precious metal of the 8th transition group (ruthenium, rhodium, palladium, osmium, iridium, platinum), and comprises at least one metal of the 2nd transition group of the Periodic Table.

Among the abovementioned precious metals, preference is given to ruthenium and very particularly to palladium. Zinc is used as preferred metal of the 2nd transition group of the Periodic Table.

Besides the precious metals mentioned and zinc, any of the catalysts used in the process of the invention may also comprise inert supports, e.g. those composed of the metals aluminum, magnesium, titanium, zirconium, and/or silicon, in the form of oxide or mixed oxide. The catalysts may optionally also comprise salts of the support metals mentioned, for example sulfates and/or phosphates. The catalysts used according to the invention may also comprise processing aids or molding auxiliaries, for example graphite.

The compositions given below are based on the reduced catalysts.

The precious metal content of the catalysts (calculated as metal) is in the range from 0.1 to 10% by weight, in particular in the range from 0.5 to 5% by weight, very particularly from 1 to 3% by weight.

The content (calculated as oxide) of metals of the 2nd transition group, e.g. zinc, in the catalysts is from 3 to 70% by weight, in particular from 10 to 50% by weight, very particularly from 20 to 30% by weight.

The process of the invention particularly preferably uses catalysts which in reduced, active form comprise at least some of the precious metal in the oxidation state 0, and which preferably comprise zinc in the oxidation state +2.

The catalysts are prepared by processes known per se, e.g. by precipitation of carbonates, impregnation of previously prepared supports, or mixing precursor compounds, and subsequent calcination.

The catalysts are advantageously converted into a form which has low resistance to flow during the hydrogenation process, for example tablets, cylinders, extrudates, or rings.

The process of the invention preferably carries out the hydrogenation in the liquid phase. The hydrogenation may be carried out continuously or batchwise on catalysts arranged in suspension or as pieces in a fixed bed. The process of the invention is preferably continuous hydrogenation of the catalyst arranged in a fixed bed, the product/starting material phase being primarily liquid under the reaction conditions.

If the hydrogenation is carried out continuously on a catalyst arranged in a fixed bed it is advantageous to convert the catalyst into the active form prior to the hydrogenation process. This may be achieved by reducing the catalyst, using hydrogen-containing gases and a temperature program. This reduction may, where appropriate, be carried out in the presence of a liquid phase which trickles over the catalyst. The liquid phase used here may comprise a solvent or the hydrogenation product.

Various versions of the process of the invention may be selected. It may be carried out under adiabatic, polytropic, or practically isothermal conditions, i.e. with a temperature rise which is typically less than 10° C., in one or more stages. In the latter case it is possible for all of the reactors, advantageously tubular reactors, to be operated under adiabatic or practically isothermal conditions, or else for one or more to be operated under adiabatic conditions and the others under practically isothermal conditions. It is also possible for the aromatic polycarboxylic esters to be hydrogenated in a straight pass or with product return.

The process of the invention is carried out in the mixed liquid/gas phase or liquid phase, concurrently in three-phase reactors, the hydrogenation gas being distributed in a manner known per se within the liquid starting material/product stream. To promote uniform liquid distribution, improved dissipation of the heat of reaction, and high space-time yield, the reactors are preferably operated with high liquid flow rates of from 15 to 120, in particular from 25 to 80, $m^3$ per $m^2$ of cross section of the empty reactor per hour. If a reactor is operated with a straight pass, the liquid hourly space velocity (LHSV) over the catalyst may be from 0.1 to 10 $h^{-1}$.

The hydrogenation may be carried out in the absence, or preferably in the presence, of a solvent. Solvents which may be used are any of the liquids which form a homogeneous solution with the starting material and product, exhibit inert behavior under hydrogenation conditions, and are easy to remove from the product. The solvent may also be a mixture of two or more substances and, where appropriate, comprise water.

Examples of substances which may be used as solvents are the following: straight-chain or cyclic ethers, such as tetrahydrofuran or dioxane, and also aliphatic alcohols whose alkyl radical has from 1 to 13 carbon atoms.

Alcohols which may preferably be used are isopropanol, n-butanol, isobutanol, n-pentanol, 2-ethylhexanol, nonanols, industrial nonanol mixtures, decanol, and industrial decanol mixtures, and tricedanols.

If alcohols are used as solvent it can be advantageous to use the alcohol or alcohol mixture which would be produced during saponification of the product. This would exclude by-product formation via transesterification. Another preferred solvent is the hydrogenation product itself.

By using a solvent it is possible to limit the concentration of aromatic compounds in the reactor feed, and the result can be better temperature control achieved in the reactor. This can minimize side-reactions and therefore increase product yield. The content of aromatic compounds in the reactor feed is preferably from 1 to 35%, in particular from 5 to 25%. In the case of reactors operated in loop mode, the desired concentration range can be adjusted via the circulation rate (quantitative ratio of returned hydrogenation discharge to starting material).

The process of the invention is carried out in the pressure range from 3 to 300 bar, in particular from 15 to 200 bar, very particularly from 50 to 200 bar. The hydrogenation temperatures are from 50 to 220° C., in particular from 100 to 200° C.

Hydrogenation gases which may be used are any desired hydrogen-containing gas mixtures in which there are no detrimental amounts present of catalyst poisons, such as carbon monoxide or hydrogen sulfide. Examples of the inert gas constituents are nitrogen and methane. It is preferable to use hydrogen at purity greater than 95%, in particular greater than 98%.

The process of the invention can convert aromatic polycarboxylic acids or derivatives of these, in particular their alkyl esters, to the corresponding alicyclic polycarboxylic compounds. In the case of the esters here, both full esters and partial esters can be hydrogenated. Full esters are compounds in which all of the acid groups have been esterified. Partial esters are compounds having at least one free acid group (or, where appropriate, one anhydride group) and at least one ester group.

The polycarboxylic esters of the invention and, respectively, the polycarboxylic esters prepared by the process of the invention preferably contain 2, 3, or 4 ester functions.

The polycarboxylic esters preferably used in the process of the invention are benzene-, diphenyl-, naphthalene- and/or anthracene polycarboxylic esters. The resultant alicyclic polycarboxylic esters are composed of one or more $C_6$ rings, where appropriate linked by a carbon-carbon bond or fused.

Use may also optionally be made of polycarboxylic esters having an underlying diphenyl oxide skeleton.

The alcohol component of the polycarboxylic esters is preferably composed of branched or unbranched alkyl, cycloalkyl, or alkoxyalkyl groups having from 1 to 25 carbon atoms. These may be identical or different within one molecule of a polycarboxylic ester, i.e. they may comprise identical or different isomers or identical or different chain lengths.

In one preferred embodiment, the present invention provides a process for the hydrogenation of benzene-1,2-, -1,3-, or -1,4-dicarboxylic esters, and/or of benzene-1,2,3-, -1,2,4-, or -1,3,5-tricarboxylic esters, i.e. the mixtures of the invention comprise the isomers of cyclohexane-1,2-, -1,3-, or -1,4-dicarboxylic esters, or of cyclohexane-1,2,3-, -1,3,5-, or -1,2,4-tricarboxylic esters.

The following aromatic carboxylic acids may be used in the process of the invention:
naphthalene-1,2-dicarboxylic acid, naphthalene-1,3-dicarboxylic acid, naphthalene-1,4-dicarboxylic acid, naphthalene-1,5-dicarboxylic acid, naphthalene-1,6-dicarboxylic acid, naphthalene-1,7-dicarboxylic acid, naphthalene-1,8-dicarboxylic acid, phthalic acid (benzene-1,2-dicarboxylic acid), isophthalic acid (benzene-1,3-dicarboxylic acid), terephthalic acid (benzene-1,4-dicarboxylic acid), benzene-1,2,3-tricarboxylic acid, benzene-1,2,4-tricarboxylic acid (trimellitic acid), benzene-1,3,5-tricarboxylic acid (trimesic acid), benzene-1,2,3,4-tetracarboxylic acid. It is also possible to use acids which are produced from the acids mentioned by using alkyl, cycloalkyl, or alkoxyalkyl groups to substitute one or more of the hydrogen atoms bonded to the aromatic core.

It is possible to use alkyl, cycloalkyl, or else alkoxyalkyl esters of the abovementioned acids, for example, these radicals encompassing, independently of one another, from 1 to 25, in particular from 3 to 15, very particularly from 8 to 13, particularly 9, carbon atoms. These radicals may be linear or branched. If a starting material has more than one ester group, these radicals may be identical or different.

Examples of compounds which may be used in the process of the invention as ester of an aromatic polycarboxylic acid are the following:
monomethyl terephthalate, dimethyl terephthalate, diethyl terephthalate, di-n-propyl terephthalate, dibutyl terephthalate, diisobutyl terephthalate, di-tert-butyl terephthalate, monoglycol terephthalate, diglycol terephthalate, n-octyl terephthalate, diisooctyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisododecyl terephthalate, ditridecyl terephthalate, di-n-octadecyl terephthalate, diisooctadecyl terephthalate, di-n-eicosyl terephthalate, monocyclohexyl terephthalate, monomethyl phthalate, dimethyl phthalate, di-n-propyl phthalate, di-n-butyl phthalate, diisobutyl phthalate, di-tert-butyl phthalate, monoglycol phthalate, diglycol phthalate, di-n-octyl phthalate, diisooctyl phthalate, di-2-ethylhexyl phthalate, di-n-nonyl phthalate, diisononyl phthalate, di-n-decyl phthalate, di-2-propylheptyl phthalate, diisodecyl phthalate, di-n-undecyl phthalate, diisoundecyl phthalate, ditridecyl phthalate, di-n-octadecyl phthalate, diisooctadecyl phthalate, di-n-eicosyl phthalate, monocyclohexyl phthalate, dicyclohexyl phthalate, monomethyl isophthalate, dimethyl isophthalate, diethyl isophthalate, di-n-propyl isophthalate, di-n-butyl isophthalate, diisobutyl isophthalate, di-tert-butyl isophthalate, monoglycol isophthalate, diglycol isophthalate, di-n-octyl isophthalate, diisooctyl isophthalate, 2-ethylhexyl isophthalate, di-n-nonyl isophthalate, diisononyl isophthalate, di-n-decyl isophthalate, diisodecyl isophthalate, di-n-undecyl isophthalate, diisododecyl isophthalate, di-n-dodecyl isophthalate, ditridecyl isophthalate, di-n-octadecyl isophthalate, diisooctadecyl isophthalate, di-n-eicosyl isophthalate, monocyclohexyl isophthalate.

It is also possible to use mixtures made from two or more polycarboxylic esters. Mixtures of this type may be obtained in the following ways, for example:
a) a polycarboxylic acid is partially esterified using an alcohol in such a way as to give both full and partial esters.
b) A mixture of at least two polycarboxylic acids is esterified using an alcohol, producing a mixture of at least two full esters.
c) A polycarboxylic acid is treated with an alcohol mixture, and the product can be a mixture of many full esters.
d) A polycarboxylic acid may also be partially esterified using an alcohol mixture.
e) A mixture of at least two carboxylic acids may also be partially esterified using an alcohol mixture.
f) A mixture of at least two polycarboxylic acids may also be partially esterified using an alcohol mixture.

Instead of the polycarboxylic acids in reactions a) to f), use may also be made of their anhydrides.

Aromatic esters are often prepared industrially from alcohol mixtures, in particular the full esters by route c).

Examples of corresponding alcohol mixtures are:

$C_5$ alcohol mixtures prepared from linear butenes by hydroformylation followed by hydrogenation;

$C_5$ alcohol mixtures prepared from butene mixtures which comprise linear butene and isobutene, by hydroformylation followed by hydrogenation;

$C_6$ alcohol mixtures prepared from a pentene or from a mixture of two or more pentenes, by hydroformylation followed by hydrogenation;

$C_7$ alcohol mixtures prepared from triethylene or dipropene or from a hexeneisomer or from some other mixture of hexeneisomers, by hydroformylation followed by hydrogenation;

$C_8$ alcohol mixtures, such as 2-ethylhexanol (2 isomers), prepared by aldol condensation of n-butyraldehyde followed by hydrogenation;

$C_9$ alcohol mixtures prepared from $C_4$ olefins by dimerization, hydroformylation, and hydrogenation. The starting materials here for preparing the $C_9$ alcohols may be isobutene or a mixture of linear butenes or mixtures of linear butenes and isobutene. The $C_4$ olefins may be dimerized with the aid of various catalysts, such as protonic acids, zeolites, organometallic nickel compounds, or solid nickel-containing catalysts. The $C_8$ olefin mixtures may be hydroformylated with the aid of rhodium catalysts or cobalt catalysts. There is therefore a wide variety of industrial $C_9$ alcohol mixtures.

$C_{10}$ alcohol mixtures prepared from tripropylene by hydroformylation followed by hydrogenation; 2-propylheptanol (2 isomers) prepared by aldol condensation of valeraldehyde followed by hydrogenation;

$C_{10}$ alcohol mixtures prepared from a mixture of at least two $C_5$ aldehydes by aldol condensation followed by hydrogenation;

$C_{13}$ alcohol mixtures prepared from hexaethylene, tetrapropylene, or tributene, by hydroformylation followed by hydrogenation.

Other alcohol mixtures may be obtained by hydroformylation followed by hydrogenation from olefins or olefin mixtures which arise in Fischer-Tropsch syntheses, in the dehydrogenation of hydrocarbons, in metathesis reactions, in the polygas process, or in other industrial processes, for example.

Olefin mixtures with olefins of differing carbon numbers may also be used to prepare alcohol mixtures.

The process of the invention can use any ester mixture prepared from aromatic polycarboxylic acids and from the abovementioned alcohol mixtures. According to the invention, preference is given to esters prepared from phthalic acid or phthalic anhydride and from a mixture of isomeric alcohols having from 6 to 13 carbon atoms.

Examples of industrial phthalates which can be used in the process of the invention are products with the following tradenames:

Vestinol C (di-n-butyl phthalate) (CAS No. 84-74-2); Vestinol IB (diisobutyl phthalate) (CAS No. 84-69-5); Jayflex DINP (CAS No. 68515-48-0); Jayflex DIDP (CAS No. 68515-49-1); Palatinol 9P (68515-45-7), Vestinol 9 (CAS No. 28553-12-0); TOTM (CAS No. 3319-31-1); Linplast 68-TM, Palatinol N (CAS No. 28553-12-0); Jayflex DHP (CAS No. 68515-50-4); Jayflex DIOP (CAS No. 27554-26-3); Jayflex UDP (CAS No. 68515-47-9); Jayflex DIUP (CAS No. 85507-79-5); Jayflex DTDP (CAS No. 68515-47-9); Jayflex L9P (CAS No. 68515-45-7); Jayflex L911P (CAS No. 68515-43-5); Jayflex L11P (CAS No. 3648-20-2); Witamol 110 (CAS No. 68515-51-5); Witamol 118 (Di-n-C8-C10-alkyl phthalate) (CAS No. 71662-46-9); Unimoll BB (CAS No. 85-68-7); Linplast 1012 BP (CAS No. 90193-92-3); Linplast 13XP (CAS No. 27253-26-5); Linplast 610P (CAS No. 68515-51-5); Linplast 68 FP (CAS No. 68648-93-1); Linplast 812 HP (CAS No. 70693-30-0); Palatinol AH (CAS No. 117-81-7); Palatinol 711 (CAS No. 68515-42-4); Palatinol 911 (CAS No. 68515-43-5); Palatinol 11 (CAS No. 3648-20-2); Palatinol Z (CAS No. 26761-40-0); Palatinol DIPP (CAS No. 84777-06-0); Jayflex 77 (CAS No. 71888-89-6); Palatinol 10 P (CAS No. 533-54-0); Vestinol AH (CAS No. 117-81-7).

Reference is made below to the possible stereoisomers of the alicyclic system, the trans form being differentiated from the cis form. For example, as mentioned above, in the case of cyclohexane-1,2-dicarbocylic esters the trans forms are the compounds in which the ester groups have either axial-axial (a,a) or equatorial-equatorial (e,e) orientation. In the cis compounds one ester group has axial (a) orientation and the other has equatorial (e) orientation. As stated above, other orientations may apply for distinguishing between these two forms in the case of other alicyclic polycarboxylic esters.

In particular versions of the process of the invention, dinonyl phthalates or a mixture of isomeric dinonyl phthalates is/are hydrogenated to give a mixture of isomeric dinonyl cyclohexane-1,2-dicarboxylates, the proportion of the cis isomer with respect to the position of the carboxy groups on the cyclohexane ring being above 93 mol %.

Similarly, di(2-ethylhexyl) phthalates may be reacted to give di(2-ethylhexyl)cyclohexane-1,2-dicarboxylates, or didecyl phthalates may be reacted to give didecyl cyclohexane-1,2-dicarboxylates. With respect to the cis/trans isomers, what has been said for the isononyl ester is again applicable.

The mixtures of the invention or mixtures prepared according to the invention comprise above 93 mol %, based on the entire amount of ester, of cis compound(s). The mixtures preferably comprise from 94 to 100 mol %, from 95 to 100 mol %, from 96 to 100 mol %, from 97 to 100 mol %, from 98 to 100 mol %, or from 99 to 100 mol %, of the cis isomer(s).

The present invention also provides the use of the alicyclic polycarboxylic esters of the invention or prepared according to the invention as a plasticizer in plastics. Preferred plastics are PVC, homo- and copolymers based on ethylene, on propylene, on butadiene, on vinyl acetate, on glycidyl acrylate, on glycidyl methacrylate, on acrylates, or on acrylates having, bonded to the oxygen atom of the ester group, alkyl radicals of branched or unbranched alcohols having from one to ten carbon atoms, or on styrene or on acrylonitrile, and homo- or copolymers of cyclic olefins. The following plastics may be mentioned as representatives of the above groups:

polyacrylates having identical or different alkyl radicals having from 4 to 8 carbon atoms, bonded to the oxygen atom of the ester group, in particular having the n-butyl, n-hexyl, n-octyl, or 2-ethylhexyl radical, polymethacrylate, polymethyl methacrylate, methyl acrylate-butyl acrylate copolymers, methyl methacrylate-butyl methacrylate copolymers, ethylene-vinyl acetate copolymers, chlorinated polyethylene, nitrile rubber, acrylonitrile-butadiene-styrene copolymers, ethylene-propylene copolymers, ethylene-propylene-diene copolymers, styrene-acrylonitrile copolymers, acrylonitrile-butadiene rubber, styrene-butadiene elastomers, and methyl methacrylate-styrene-butadiene copolymers.

The alicyclic polycarboxylic esters of the invention may moreover be used to modify plastics mixtures, for example the mixture of a polyolefin with a polyamide.

The present invention also provides mixtures made from plastics with the alicyclic polycarboxylic esters of the invention, or prepared according to the invention. Suitable plastics are the abovementioned compounds. These mixtures preferably comprise at least 5% by weight, particularly preferably from 20 to 80% by weight, very particularly preferably from 30 to 70% by weight, of the alicyclic polycarboxylic esters.

Mixtures made from plastics, in particular PVC, and comprising one or more of the alicyclic polycarboxylic esters of the invention, may be present in the following products, for example:

casings for electrical devices, such as kitchen appliances, computer cases, casings and components of phonographic and television equipment, of piping, of apparatus, of cables, of wire sheathing, of insulating tapes, of window profiles, in interior decoration, in vehicle construction and furniture construction, plastisols, in floor coverings, medical products, packaging for food or drink, gaskets, films, composite films, phonographic disks, synthetic leather, toys, containers for packaging, adhesive-tape films, clothing, coatings, and fibers for fabrics.

Mixtures made from plastics, in particular PVC, and comprising one or more of the alicyclic polycarboxylic esters of the invention may moreover be used for producing the following products, for example:

a casing for electrical devices, piping, apparatus, a cable, wire sheathing, a window profile, a floor covering, a medical product, a toy, packaging for food or drink, a gasket, a film, a composite film, a phonographic disk, synthetic leather, a container for packaging, an adhesive-tape film, clothing, a coating, or a fiber for fabrics.

Besides the abovementioned applications, the alicyclic polycarboxylic esters of the invention may be used as a component in lubricating oil, or as a constituent of coolants or metal working fluids.

The examples below are intended to illustrate the invention without restricting the scope of protection defined by the patent claims.

Analysis:

The ratio of cis- and trans-cyclohexane-1,2-dicarboxylic diesters was determined by $^1$H NMR spectroscopy.
Measuring device: Avance DPX-360 NMR spectrometer from the company Bruker
Measurement frequency: 360 MHz
Sample head: QNP sample head, 5 mm
Solvent: $CDCl_3$ (degree of deuteration 99.8%)
Standard: Tetramethylsilane (TMS)
Measurement temperature: 303 K
Number of scans: 32
Delay: 1 s
Acquisition time: 4.4 s
Spectral width: 7440.5 Hz
Pulse angle: 30°
Pulse length: 3.2 µs An example of the method of recording the $^1$H NMR spectra comprised dissolving about 20 mg of the specimen in about 0.6 ml of $CDCl_3$ (with 1% by weight of TMS). The spectra were recorded under the conditions given above and referenced to TMS=0 ppm.

In the $^1$H NMR spectra obtained, the methyne signals for dialkyl cis- and trans-hexahydrophthalates could be distinguished with chemical shifts of about 2.8 ppm and 2.6 ppm, respectively, the signal shifted toward lower field corresponding to the cis compound (larger ppm value). To quantify the isomers, the integrals were determined from 3.0 ppm to 2.7(2) ppm and from 2.7(2) ppm to 2.5 ppm, the two integrals being separated in the middle between the signals. The ratio of the two isomeric structures could be determined from the intensity ratios.

EXAMPLE 1

Comparative Example

The catalyst used comprised catalyst H 14184 (0.5% of Ag on transition alumina in the form of extrudates of diameter 1.2 mm) from Degussa. 57 g of catalyst were placed in a rotating basket in a stirred autoclave and reduced in accordance with the manufacturer's instruction in hydrogen at 4 bar and 200° C. The autoclave was then filled with 600 g of diisononyl phthalate (abbreviated to DINP, the product Vestinol 9 from Oxeno GmbH), and hydrogen was applied at a pressure of 200 bar. Hydrogenation was then carried out at a temperature of 120° C. for 70 hours. DINP conversion was complete. The proportion of diisononyl cis-cyclohexanedicarboxylate (cis-DINCH) in the product was found to be 85%, the remainder being trans-DINCH.

EXAMPLE 2

Comparative Example

The experiment of example 1 was repeated, except that in this the reaction temperature was raised to 200° C. and the hydrogenation time shortened to 21.2 h. Conversion was again complete, but this time the cis-DINCH content was only 81.4%. Although the very high reaction temperature achieved a high reaction rate, isomeric selectivity reduced markedly.

EXAMPLE 3

Inventive

The catalyst used comprised catalyst H 14184 (0.5% of Pd on transition alumina in the form of extrudates of diameter 1.2 mm) from Degussa AG, which had also been doped with 2% ZnO. 59 g of catalyst were placed in a rotating basket in a stirred autoclave and reduced in accordance with the manufacturer's instruction in hydrogen at 4 bar and 200° C. The autoclave was then filled with 600 g of diisononyl phthalate (abbreviated to DINP, the product Vestinol 9 from Oxeno GmbH), and hydrogen was applied at a pressure of 200 bar. Hydrogenation was then carried out at a temperature of 120° C. for 60 hours. DINP conversion was complete. The proportion of diisononyl cis-cyclohexanedicarboxylate (cis-DINCH) in the product was found to be 97.2%, the remainder being trans-DINCH.

EXAMPLE 4

Comparative Example

The catalyst used comprised 1.0% of Ru on $\square$-$Al_2O_3$ in the form of beads of diameter 3 mm. 74 g of catalyst were placed in a rotating basket in a stirred autoclave and reduced in accordance with the manufacturer's instruction in hydrogen at 4 bar and 200° C. The autoclave was then filled with 600 g of diisononyl phthalate (abbreviated to DINP, the product Vestinol 9 from Oxeno GmbH), and hydrogen was applied at a pressure of 200 bar. Hydrogenation was then carried out at a temperature of 120° C. for 22 hours. DINP conversion was complete. The proportion of diisononyl cis-cyclohexanedicarboxylate (cis-DINCH) in the product was found to be 93.6%, the remainder being trans-DINCH.

EXAMPLE 5

Inventive

The experiment of example 4 was repeated under the same conditions, except that in this case use was made of a catalyst which had also been doped with 2.5% of ZnO. Conversion was again complete, and cis-DINCH content was 97.3%.

What is claimed is:

1. A process for preparing alicyclic polycarboxylic acid ester isomer mixtures, which comprises:
   hydrogenating an aromatic polycarboxylic acid ester isomer in the presence of catalyst which comprises at least one precious metal of the 8$^{th}$ transition Group and at least one metal of the 2nd transition Group of the Periodic Table, wherein the alicyclic polycarboxylic acid ester isomer mixture produced comprises above 93 mol % amount of the cis isomer.

2. The process as claimed in claim 1, wherein the hydrogenation is conducted at a temperature ranging from 50 to 220° C. and at a pressure ranging from 3 to 300 bar.

3. The process as claimed in claim 1, wherein the aromatic polycarboxylic acid esters are benzene- or biphenylpolycarboxylic acid esters, diphenyl oxide polycarboxylic esters, or naphthalene- or anthracenepolycarboxylic acid esters.

4. The process as claimed in claim 1, wherein the polycarboxylic acid esters have 2, 3 or 4 ester groups.

5. The process as claimed in claim 1, wherein the alcohol components of the polycarboxylic acid esters are alkoxyalkyl, cycloalkyl, and/or alkyl groups having from 1 to 25 carbon atoms, branched or unbranched, and in each instance identical or different.

* * * * *